(12) United States Patent
Bloom, Jr.

(10) Patent No.: US 6,412,494 B1
(45) Date of Patent: Jul. 2, 2002

(54) ASPIRATING AND VOLATILIZING LIQUID DISPENSER

(76) Inventor: Walter L. Bloom, Jr., 841 Peachtree Hills Cir., Atlanta, GA (US) 30305-4249

( * ) Notice: Subject to any disclaimer, the term of this patent is extended or adjusted under 35 U.S.C. 154(b) by 0 days.

(21) Appl. No.: 09/525,977

(22) Filed: Mar. 15, 2000

(51) Int. Cl.$^7$ ................................................ A24F 47/00
(52) U.S. Cl. ............. 131/273; 128/200.14; 128/200.21; 222/511; 222/522
(58) Field of Search ...................... 131/273; 128/200.14, 128/200.21; 222/522, 511

(56) References Cited

U.S. PATENT DOCUMENTS 4,993,436 A * 2/1991 Bloom, Jr. .................. 131/335
6,155,268 A * 12/2000 Takeuchi ..................... 131/273

* cited by examiner

Primary Examiner—Christopher A. Fiorilla
(74) Attorney, Agent, or Firm—Gardner Groff & Mehrman, P.C.

(57) ABSTRACT

A device for controllably dispensing and volatilizing liquid by the user sucking or drawing on the device. An elongate tube defines a reservoir for liquid and air bounded by a solid and a porous plug, and an aperture for the flow of air that is positioned between said porous plug and the open end of the device. A mechanical means of controlling the surface area of said aperture is provided. Three preferred embodiments of said mechanical means include a pleated section with holes in the troughs of pleats, a rotating sleeve about an ovular slit, and a translating tubular insert into the open end of a device with an aperture consisting of a series of holes.

14 Claims, 2 Drawing Sheets

ASPIRATING AND VOLATILIZING LIQUID DISPENSER

TECHNICAL FIELD

This invention relates generally to dispensing devices and more particularly to a device for controllably dispensing and volatilizing liquid by the user sucking or drawing on the device.

BACKGROUND OF THE INVENTION

U.S. Pat. No. 4,993,436 was issued to this inventor on Feb. 19, 1991 for a hand-held dispensing and volatilizing device with reciprocal on/off control of air and liquid flows. Specifically, when a user blocks the device's solitary air vent passage, the user can draw liquid from a reservoir by sucking. In contrast, when the solitary vent passage is unblocked, sucking draws air through the passage while drawing very little, if any, liquid from the reservoir. Further, in order to block the solitary air vent passage it is necessary for a user to cover the passage, for example with a finger.

The aforesaid control mechanism is somewhat crude. Consequently, a need yet remains for a hand-held aspirating and volatilizing device with a more a more refined and variable control of both air and liquid flows.

SUMMARY OF THE INVENTION

Briefly described, the present invention comprises a flexible sipping straw that a) has a solid plug inserted at the end of the straw which is farther from the straw's flexible, pleated portion, b) has a porous plug inserted immediately above the flexible, pleated portion toward the solidly plugged end of the straw, and c) has a row of holes punched one per pleat in the trough of each pleat of the flexible portion of the straw. Thus, on one hand when all of the pleats are closed, the user can draw no air, but only liquid from the straw. On the other hand, as the user opens successive pleats, the ratio of air to liquid increases that the user can draw by sucking on the open end of the straw.

In a first preferred embodiment, the aperture and mechanical means of controlling the surface area of the aperture comprise a pleated section of the tube, wherein each pleat within the pleated section has both a crest and a trough, and wherein holes of suitable diameter are positioned in the trough of at least one of the pleats so that the ratio of air to liquid that may be drawn by a user sucking on the open end of said tube will depend directly on the number of pleats with holes in their troughs that are pulled open at any given time.

In a second preferred embodiment, the aperture comprises an opening such as an elongate slit or a series of holes and the mechanical means of controlling the surface area of said aperture comprises a partially open sleeve that encloses the aperture, which sleeve may be rotated about the cylindrical axis of the tubular body of the device so as to cover or uncover all or a portion of said aperture.

In a third preferred embodiment, the aperture comprises an opening such as an elongate slit or a series of holes, and the mechanical means of controlling the surface area of said aperture comprises either an external sleeve or an insert into the open end of the tubular body of the device, which sleeve or insert may be translated with respect to the cylindrical axis of the tubular body of the device so as to cover or uncover all or a portion of said aperture.

In operation, when the aperture is closed, the user can draw no air and only liquid from said tube by sucking on the open end of said tube. The amount of liquid that a user can draw out by sucking continuously at any one time is limited, however, by the fact that, in the absence of back-drafting of air through the porous plug into the reservoir, a vacuum develops in the reservoir as liquid is drawn out such that a single charge is created.

On the other hand, as the user opens or uncovers more and more of the aperture, the ratio of air to liquid increases that the user can draw by sucking on the open end of the tube. If the aperture is completely open then very little liquid, if any, may be drawn out of the reservoir. Nevertheless, volatilization of residual droplets of liquid that remain in the tube between the porous plug and the open end of the tube may create the sensation flavor even when no liquid is being drawn through the porous plug.

BRIEF DESCRIPTIONS OF THE DRAWINGS

Figure 6:

FIGS. 6A–C are detailed drawings of the aperture and aperture control mechanism of the second embodiment of the device shown in 3 different settings.

Figure 7:
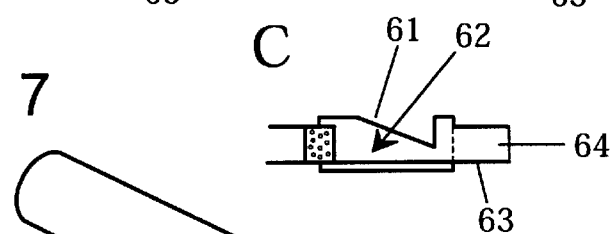

FIG. 7 is a perspective view of a third embodiment of the device.

Figure 8:
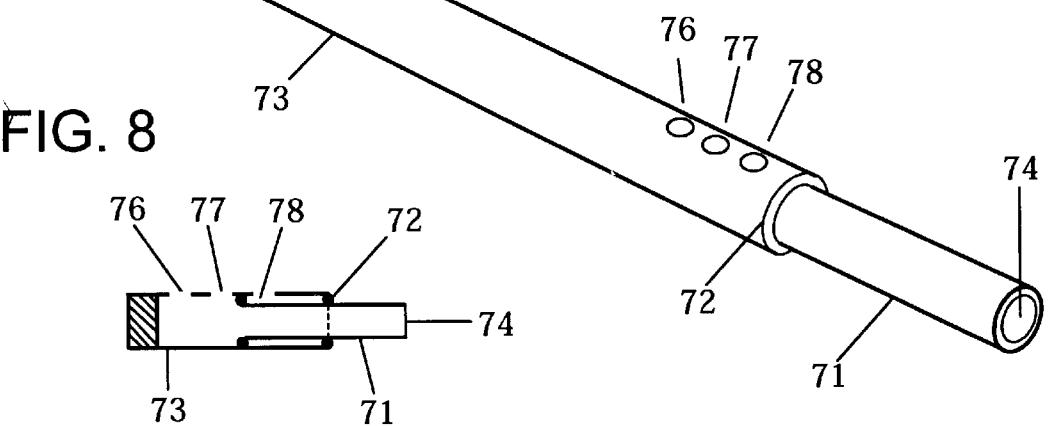

FIG. 8 is a detailed cross-section of the aperture and aperture control mechanism of the third embodiment of the device configured for part liquid and part air flows.

DETAILED DESCRIPTION OF THE PREFERRED EMBODIMENTS

Figure 1:
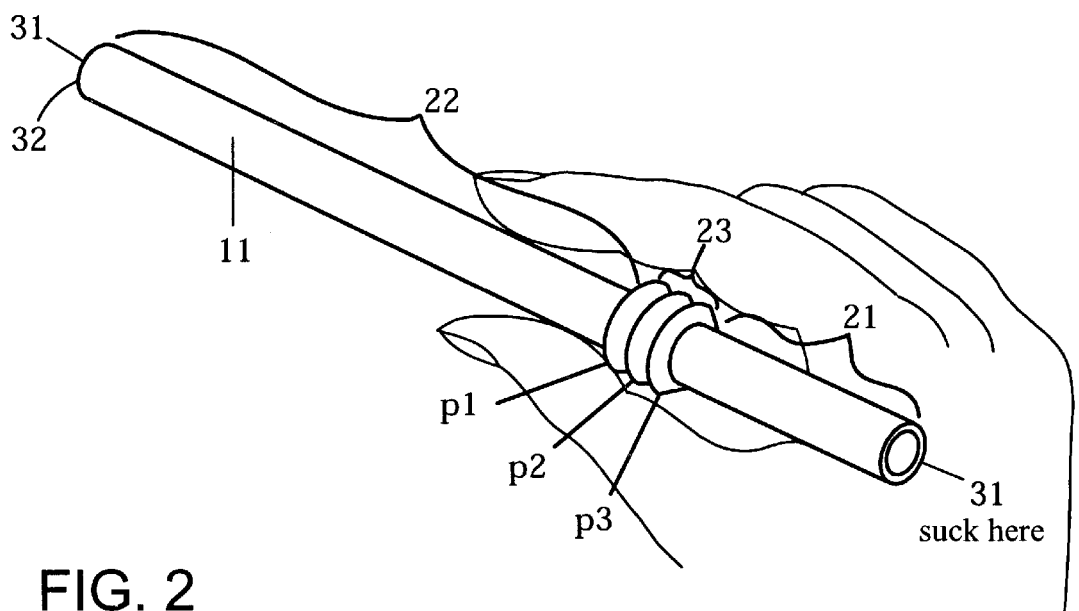
FIG. 1 is a perspective view of a first embodiment of the device according to a preferred form of the invention and as shown being held between two fingers.

FIG. 1 shows a first preferred embodiment of the device being held in one hand by a user. As it appears, elongate tube 11 is divided into three sections—namely a first unpleated section 21 that is separated from a second unpleated section 22 by a pleated section 23. The inventor notes that the general form of the tube is the same as that of a flexible drinking straw. FIG. 1 also shows that the tube 11 may have an open end 32 with a solid plug 31 inserted into it. Further, the illustrated embodiment of FIG. 2 shows pleated section 23 as having three folding pleats p1, p2, and p3, where each pleat has both a crest and a trough, and where hole h1 is positioned in the trough between the crests of pleats p1 and p2, and hole h2 is positioned in the trough between the crests of pleats p2 and p3, and where all three of the holes are aligned with respect to the cylindrical axis of hollow tube 11.

Figure 2:
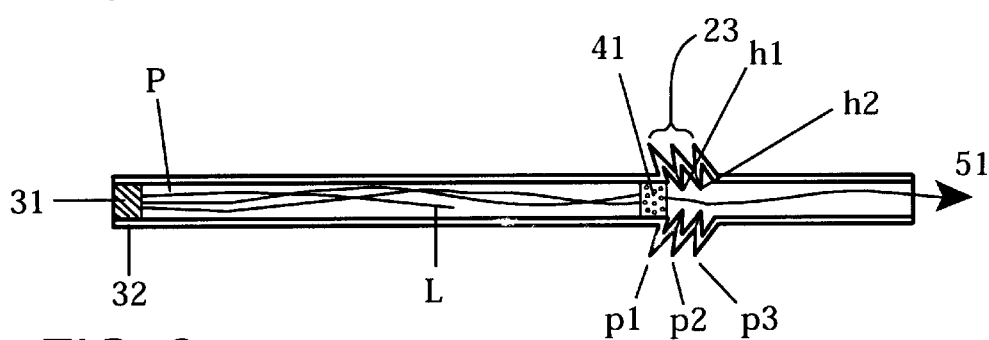
FIG. 2 is a cross section of the first embodiment of the device along its cylindrical axis with the device configured for liquid flow only.

FIG. 2 shows a cross section of said first preferred embodiment with the device configured for liquid flow only. A flow control member such as porous plug 41 is inserted into hollow tube 11 so that it abuts that end of pleated section 23 that is closer to the plugged end 32 of the second unpleated section 22. The inventor notes that the trough of pleat p3 prevents the porous plug 41 from moving any farther away from solid plug 31. A liquid L that is suitable for human consumption also has been inserted into the reservoir formed by that portion of hollow tube 11 between porous plug 41 and solid plug 31. As illustrated, a small air pocket P separates solid plug 31 from liquid L.

FIG. 2 also shows the preferred embodiment configured so as to provide flows of liquid only when a user sucks on open end 51 of the device. Since all three pleats p1, p2, and p3 are closed, both holes h1 and h2 are blocked, and, consequently, no air can flow through either of the holes when a user sucks on open end 51 of the device. As a result, a user's sucking draws a quantity of liquid through porous plug 41, which quantity is limited by the diameter d of hollow tube 11 and by the vacuum that develops in the tube between porous plug 41 and solid plug 31 in response to the user's sucking.

Figure 3:
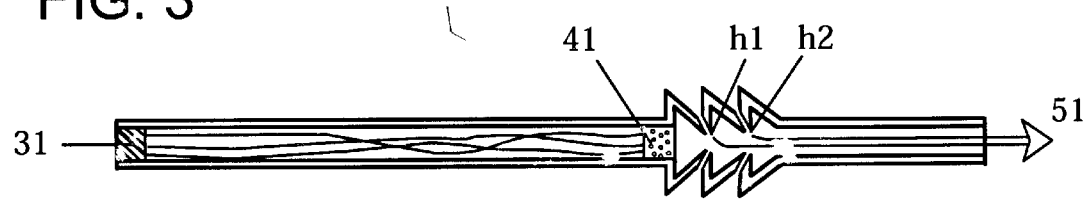
FIG. 3 is a cross section of the first embodiment of the device along its cylindrical axis with the device configured for air flow only.

FIG. 3 then shows the first preferred embodiment configured so as to provide flows of air only when a user sucks on open end 51 of the device. Since all three pleats p1, p2, and p3 are open, both holes h1 and h2 are unblocked, and, consequently, air can flow through both holes when a user sucks on open end 51 of the device. The diameter of the two holes is selected so that a user's sucking draws air through the holes but draws no liquid through porous plug 41, where the quantity of air drawn in a single inhalation is limited only by the lung capacity of the user.

Figure 4:
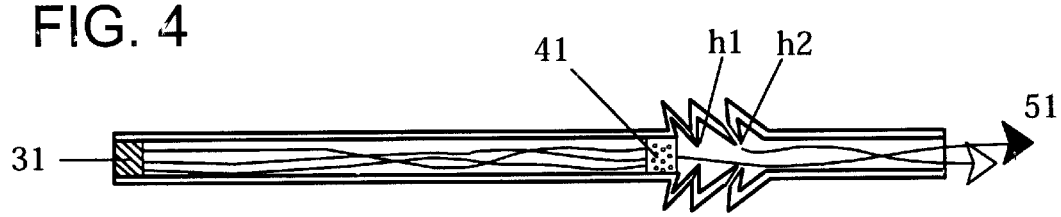
FIG. 4 is a cross section of first embodiment of the device along its cylindrical axis with the device configured for part liquid and part air flows.

FIG. 4 shows the first preferred embodiment configured so as to provide flows of both liquid and air when a user sucks on open end 51 of the device. In the configuration shown, only one air hole is open and the diameter of that hole is selected so that a user's sucking draws a small amount of liquid and a less than free flow of air.

Figure 5:
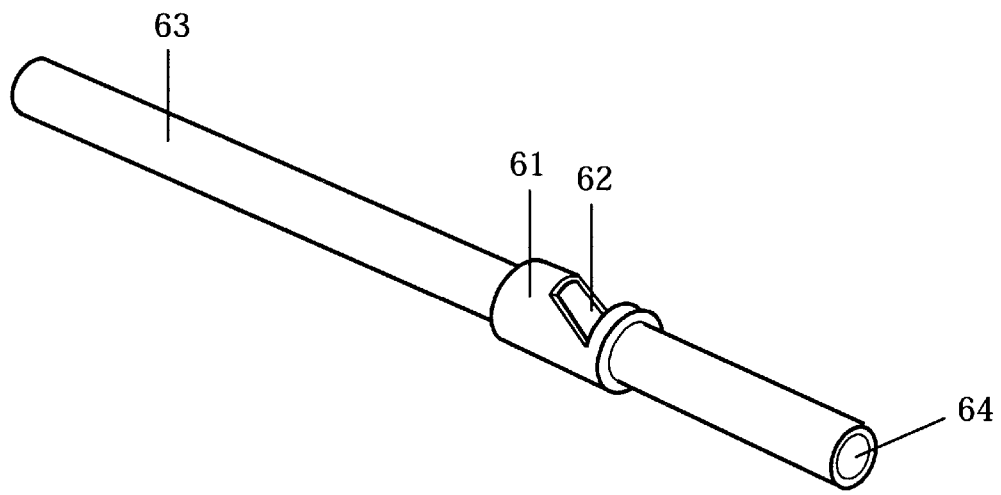
FIG. 5 is a perspective view of a second embodiment of the device.

FIG. 5 shows a second preferred embodiment of the invention with a rotating sleeve 61 that can be rotationally positioned so as to control the ratio of liquid to air that flows in response to a user's sucking. FIG. 6A shows a detail of said rotating sleeve 61 that is set in a position that completely covers aperture 62, which aperture is in the form of an elongate ovular slit in tube 63, and that produces limited flows only of liquid in response to a user's sucking on open end 64 of the tube 63. FIG. 6B shows a detail of said rotating sleeve 61 set in a position that partially covers aperture 62 so as to produce partial flows of both liquid and air in response to a user's sucking. FIG. 6C shows a detail of said rotating sleeve 61 set in a position that completely uncovers aperture 62 so as to produce flows only of air in response to a user's sucking, which flows are limited in volume by a user's lung capacity.

FIG. 7 shows a third preferred embodiment of the invention with a translating tubular insert 71 that is inserted in the open end 72 of hollow tube 73 and can be used to control the ratio of liquid to air that flows in response to a user's sucking on open end 74 of the translating tubular insert 71. FIG. 8 shows a detail of the aperture, which consists of a series of three holes 76, 77, and 78, with translating tubular insert 71 positioned so as to provide partial flows of both liquid and air in response to a user's sucking.

While the invention has been shown and described in preferred forms, it will be apparent to those skilled in the art that many modifications, additions, and deletions can be made therein without departing from the spirit and scope of the invention as set forth in the following claims.

I claim:

1. A liquid dispensing and volatilizing device, comprising:

an elongate tubular body having an open portion and defining a reservoir for holding liquid and air;

a fluid flow control member disposed between the reservoir and the open portion of the tubular body;

one or more apertures for the flow of air, the apertures defined in the tubular body between the fluid flow control member and the open portion; and one or more pleats in the tubular body, each of the pleats having a crest and a trough, and wherein at least one of the apertures is positioned in the trough of at least one of the pleats so that the ratio of air to liquid that may be drawn by a user sucking on the open portion of the tubular body will depend on the number of pleats with apertures in their troughs that are pulled open at any given time.

2. The device as claimed in claim 1 wherein the fluid flow controller comprises a porous plug.

3. The device as claimed in claim 1 wherein the tubular body has an open end and further comprising a plug removably received in the open end.

4. A liquid dispensing and volatilizing device, comprising:

an elongate tubular body having an open portion and defining a reservoir for holding liquid and air;

a fluid flow control member disposed between the reservoir and the open portion of the tubular body;

at least one aperture for the flow of air, the aperture defined in the tubular body between the fluid flow control member and the open portion; and an external or internal sleeve that may be rotated about the cylindrical axis of the tubular body to cover or uncover all or a portion of the aperture.

5. The device as claimed in claim 4 wherein the aperture comprises an elongate ovular slit.

6. The device as claimed in claim 4 wherein the fluid flow controller comprises a porous plug.

7. The device as claimed in claim 4 wherein the tubular body has an open end and further comprising a plug removably received in the open end.

8. The device as claimed in claim 4 wherein the sleeve has an aperture defined therein that is alignable with the aperture in the tubular body.

9. The device as claimed in claim 4 wherein the aperture comprises a frusto-conical slit.

10. A liquid dispensing and volatilizing device, comprising:

an elongate tubular body having an open portion and defining a reservoir for holding liquid and air;

a fluid flow control member disposed between the reservoir and the open portion of the tubular body;

at least one aperture for the flow of air, the aperture defined in the tubular body between the fluid flow control member and the open portion, the aperture comprising an elongate ovular slit or a series of holes; and an external or internal sleeve that may be translated with respect to the cylindrical axis of the tubular body to cover or uncover all or a portion of said aperture.

11. The device as claimed in claim 10 wherein the aperture comprises a series of holes.

12. The device as claimed in claim 10 wherein the fluid flow controller comprises a porous plug.

13. The device as claimed in claim 10 wherein the tubular body has an open end and further comprising a plug removably received in the open end.

14. The device as claimed in claim 10 wherein the sleeve has an aperture defined therein that is alignable with the aperture in the tubular body.

* * * * *